United States Patent [19]
Nestler et al.

[11] Patent Number: 5,556,837
[45] Date of Patent: Sep. 17, 1996

[54] METHODS FOR TREATING ADDICTIVE DISORDERS

[75] Inventors: Eric J. Nestler, Cheshire; Melissa T. Berhow, New Haven, both of Conn.; Dana Beitner-Johnson, Rockville, Md.; David S. Russell, Branford, Conn.; Ronald M. Lindsay, Briarcliff Manor, N.Y.

[73] Assignees: Regeneron Pharmaceuticals Inc., Tarrytown, N.Y.; Yale University, New Haven, Conn.

[21] Appl. No.: 283,700

[22] Filed: Aug. 1, 1994

[51] Int. Cl.⁶ .................................................. A61K 38/17
[52] U.S. Cl. .......................... 514/21; 424/570; 514/811; 514/812; 514/813
[58] Field of Search ............................ 514/21, 811, 812, 514/813; 424/570

[56] References Cited

U.S. PATENT DOCUMENTS

| | | | |
|---|---|---|---|
| 5,169,764 | 12/1992 | Shooter et al. | 435/69.7 |
| 5,180,820 | 1/1993 | Barde et al. | 536/23.51 |
| 5,229,500 | 7/1993 | Barde et al. | 530/399 |

FOREIGN PATENT DOCUMENTS

WO93/25684  12/1993  WIPO .

OTHER PUBLICATIONS

Berhow et al., 1994, Soc. Neurosci. Abst. 20:454.18.
Fandl et al., 1994, J. Biol. Chem. 269:755–759.
Hyman et al., 1994, J. Neurosci. 14:335–347.
Lindsay et al., 1994, TINS 17:182–90.
Beitner–Johnson et al., 1993, Soc. Neurosci. Abst. 19:663.
Ip et al., 1993, J. Neuroscience 13:3394–3405.
Ip et al., 1993, Neuron 10:89–102.
Nestler et al., 1993, Neuron 11:995–1006.
Lindsay et al., 1993, Experimental Neurology 124:103–118.
Wong et al., 1993, European J. Neuroscience 5:466–474.
Ip et al., 1992, Proc. Natl. Acad. Sci. USA 89:3060–3064.
Langer, 1990, Science 249:1527–1533.
Lindsay and Rohrer, 1985, Develop. Biol. 112:30–48.
Barde et al., 1982, EMBO J. 1:549–553.
Barde et al., 1980, Proc. Natl. Acad. U.S.A. 77:1199–1203.

*Primary Examiner*—Brian Burn
*Attorney, Agent, or Firm*—Klauber & Jackson

[57] ABSTRACT

The present invention is broadly directed to treatment of an addictive disease or disorder. In particular, the invention relates to inhibiting or reversing the biochemical and neurophysiological changes that correlate with behavioral changes of addictive diseases or disorders. The method of the invention comprises administering to a subject suspected of suffering from an addictive disease or disorder an amount of brain-derived factor (BDNF) or neurotrophin-4 (NT-4), or both, effective to reverse behavioral changes that are associated with the addictive disease or disorder. In a specific Example, administration of BDNF or NT-4 inhibits or reverses increased expression of tyrosine hydroxylase and glial ibrillary acidic protein in the ventral tegmental area of the brain, and inhibits or reverses increased levels of cyclic-AMP-dependent protein kinase activity in the nucleus accumbens.

20 Claims, 3 Drawing Sheets

METHODS FOR TREATING ADDICTIVE DISORDERS

The research leading to the present invention was supported with funds from a National Institute of Drug Abuse grant. The government may have certain rights in the invention.

FIELD OF THE INVENTION

The present invention is broadly directed to treatment of an addictive disease or disorder. More particularly, the invention relates to inhibiting or reversing the biochemical and neurophysiological changes that correlate with behavioral changes of addictive diseases or disorders.

BACKGROUND OF THE INVENTION

Neurophysiological Consequences of Addictive Disorders

Drug abuse endures as one of the major public health problems in the United States, and throughout the world. One of the core features of addictive disorders, in laboratory animals as well as in humans, is that drugs of abuse are acutely reinforcing and produce intense drug craving following chronic exposure. Behavioral and pharmacological studies have implicated the mesolimbic dopamine system (containing the ventral tegmental area [VTA] and its projections, e.g., the nucleus accumbens [NAc]) in the acute reinforcement and craving seen with opiates, cocaine, alcohol, and other drugs of abuse. An important goal of research in this area is to identify changes that drugs of abuse produce in this neural pathway that account for the intense craving seen with chronic drug use, and more critically, to identify factors that can inhibit or reverse these changes to the neural pathway.

Over the past several years, studies have identified a series of common and specific actions of opiates, cocaine, and alcohol on the mesolimbic dopamine system (see, Nestler et al., 1993, Neuron 11:995–1006). In the VTA, these actions include increased levels of tyrosine hydroxylase (TH) and glial fibrillary acidic protein (GFAP), and decreased levels of neurofilaments. In the NAc, these actions include decreased levels of the inhibitory G protein, $Gi\alpha$, and increased levels of adenylyl cyclase and cyclic AMP-dependent protein kinase. Increasing direct evidence now supports a role for these various biochemical adaptations in the behavioral actions of drugs of abuse mediated via the mesolimbic dopamine system.

The finding of increased levels of glial filaments, and reduced levels of neurofilaments, in the VTA suggests that a major form of plasticity, perhaps even neural injury, occurs in this brain region during the course of chronic drug exposure. This possibility is further supported by the observation that chronic morphine or cocaine administration reduces axoplasmic transport, specifically from the VTA to the NAc (see, Nestler et al., supra).

These observations hint at the possibility that neurotrophins could possibly modify the actions of drugs of abuse on the mesolimbic dopamine system. However, there is no certainty that this is the case. Accordingly there is a need in the art to determine whether one or more neurotrophic factors can modify the actions of drugs of abuse on the brain physiology. There is a further need to identify the neurotrophin or neurotrophins, if any, that are capable of demonstrating this activity.

In a preliminary report of the present inventors (Beitner-Johnson et al., 1993, Soc. Neurosci. Abst. 19:663), various neurotrophic factors were infused via osmotic minipumps into the VTA of rats over a 10 day period. Rats were implanted with subcutaneous morphine or placebo pellets on days 5–10. Animals were sacrificed on day 11, and levels of TH, GFAP, and NFs were determined in the VTA by immunoblotting. It was found that chronic infusion of BDNF alone prior to morphine administration exerted effects opposing morphine on TH and GFAP levels. In contrast, infusion of IGF-I and CNTF prior to morphine administration exerted effects similar to those of morphine on TH and GFAP in the VTA, and NT-3 influence these proteins in a different pattern. BDNF infusion was found to decrease the ability of chronic morphine to regulate these proteins in the VTA as well as to up-regulate the cAMP pathway in the NAc, a major projection area of the VTA. These observations of changes in the VTA require confirmation in behavioral studies before reaching any firm conclusion regarding the ability of BDNF, or any neurotrophic factor, to counter the neurophysiological changes that accompany addiction in vivo. It also remained uncertain whether BDNF could affect the expression of TH and GFAP in the VTA remedially, i.e., whether this (or any) neurotrophin could reverse the changes associated with an addictive disease or disorder. Thus, there is a need in the art to determine whether the neurophysiological changes to the VTA observed in addictive diseases cause or influence the observed behavioral changes, and to demonstrate that a neurotrophin or neurotrophins that oppose the physiological changes can reverse or oppose the corresponding behavioral changes.

Brain-Derived Neurotrophic Factor

Using pig brain as a starting material, Barde et al. (1982, EMBO J. 1:549–553) reported a factor, now termed brain-derived neurotrophic factor (BDNF), which appeared to promote the survival of dorsal root ganglion neurons from E10/E11 chick embryos. The neurotrophic activity was found to reside in a highly basic protein (isoelectric point, pI>10.1) which migrated during sodium dodecyl sulfate (SDS) gel electrophoresis as a single band of 12.3 kD molecular weight. The highly basic nature and molecular size of BDNF were very similar to the NGF monomer. However, BDNF appeared to have properties that differed from the known properties of NGF in that (a) in the chick dorsal root ganglion bioassay, antibodies to NGF had no apparent effect on the biological activity of BDNF; (b) the effects of BDNF and NGF appeared to be additive; and (c) unlike NGF, BDNF was found to have no effect on the survival of E12 chick sympathetic neurons. In addition, during early studies with brain extracts, it was observed that the neurotrophic activity in these sources appeared to act upon sensory neurons at later stages of development than were associated with NGF. Using dissociated cultures of chick embryo neurons cultured on a polycationic substrate such as polylysine or polyornithine, BDNF was found to support the survival of more than 30 per cent of E10–11 (embryonic day ten or eleven) dorsal root ganglion neurons but seemed to have little effect on the survival of the same neurons at E6 (Barde et al., 1980, Proc. Natl. Acad. U.S.A. 77:1199–1203). Under similar conditions, NGF supported the survival of 30–40 percent of E6 DRG neurons. Interestingly, it was later found that when cultured on a substrate coated with the extracellular matrix glycoprotein laminin, both NGF and BDNF supported the survival of about 50 per cent of DRG neurons from chick embryos of ages E6-E12 (Lindsay et al., 1985, Develop. Biol. 112:319–328). In the latter study, the effects of NGF and BDNF were found to be additive when both were present at saturating concentrations.

Recently, ample sources of purified BDNF, nucleic acids encoding this polypeptide, and uses thereof have been disclosed in U.S. Pat. Nos. 5,229,500, issued Jul. 20, 1993 to Barde et al., and No. 5,180,820, issued to Barde et al., both of which are incorporated herein by reference in their entireties.

Neurotrophin-4 (NT-4)

NT-4 is a member of the NGF/BDNF/NT-3 family of neurotrophic factors. Xenopus, human, and rat NT-4 have been sequenced, and share all the important features that characterize the mammalian neurotrophins, although the mammalian NT-4s have many unusual features compared to the other neurotrophins (Ip et al., 1992, Proc. Natl. Acad. Sci. U.S.A. 89:3060–64). These neurotrophins demonstrate different functional characteristics. BDNF, NT-3, and NT-4, but not NGF, up-regulate the cholinergic phenotype of developing motor neurons; CNTF also stimulated cholinergic activity. Similarly, hippocampal neurons respond to BDNF, NT-3, and NT-4, but not to NGF. BDNF and NT-3 have broadly similar effects in promoting the survival and differentiated phenotype of both dopaminergic and GABAergic neurons; the effects of BDNF and NT-4 are distinct as well as overlapping toward these classes of neurons (Hyman et al., 1994, J. Neurosci. 14:335–347).

Both NT-4 and BDNF interact with the same Trk tyrosine kinase that acts as a receptor for these neurotrophins. The preferred receptor for NT-4 and BDNF is TrkB, whereas NGF preferentially binds TrkA, and NT-3 preferentially binds TrkC (Ip et al., 1993, Neuron 10:137–149). However, NT-4 interact with the TrkB receptor in a distinct fashion from BDNF, as shown by the ability of BDNF, but not NT-4, to transform cells that express a TrkB mutant (Ip et al., 1993, supra).

The citation of any reference in this application should not be construed as an admission that such reference is prior art to the instant invention.

SUMMARY OF THE INVENTION

The present invention is broadly directed to a method for treating or preventing an addictive disease or disorder, comprising administering to a subject suspected of suffering from or at risk for an addictive disease or disorder an amount of brain-derived factor (BDNF) or neurotrophin-4 (NT-4), or both, effective to reverse biochemical or physiological changes that are associated with the addictive disease or disorder. Preferably, the BDNF or NT-4 is administered intraventricularly, intracranially, or in a controlled release device that has been implanted cranially. In a preferred aspect, the BDNF or NT-4, or both, is administered continuously.

It is a particular advantage that the present invention provides, for the first time, a method and composition capable of inhibiting and reversing some of the biochemical and physiological changes, and coordinate behavioral changes, that are associated with an addictive disease or disorder in humans and in other animals. Accordingly, in a preferred aspect, the BDNF or NT-4, or both, is human. Preferably, the addictive disease or disorder is addiction to a drug of abuse. Alternatively, the addictive disease or disorder is an obsessive-compulsive disorder.

In a specific aspect, administration of BDNF or NT-4, or both, effects a neurophysiological change to the ventral tegmental area (VTA) selected from the group consisting of opposing increased levels of tyrosine hydroxylase associated with the addictive disease or disorder, opposing increased expression of glial fibrillary acidic protein associated with the addictive disease or disorder, opposing increased levels of cyclic-AMP-dependent protein kinase activity in the nucleus accumbens, and opposing decreased levels of neurofilament proteins associated with the addictive disease or disorder. In a specific example, infra, in vivo treatment of rats dosed with morphine could inhibit or reverse these biochemical changes, and associated behavioral activities.

Accordingly, it is a first object of the present invention to provide a therapeutic treatment for an addictive disease or disorder.

It is also an object of the invention to provide a prophylactic treatment for an addictive disease or disorder.

It is a particular object to provide treatment for the biochemical and physiological changes to the brain that are associated with an addictive disease or disorder.

It is a further particular object to provide treatment for the behavioral changes that correlate with such biochemical and physiological changes.

Yet another object of the invention is to provide a therapeutic or preventive treatment for an addiction to a drug of abuse.

Still another object of the invention is to treat or prevent addiction to narcotics, e.g., opiates, cocaine, nicotine, and alcohol.

These and other objects of the present invention will be more fully appreciated by reference to the accompanying detailed description of the invention.

DETAILED DESCRIPTION OF THE INVENTION

Figure 1:
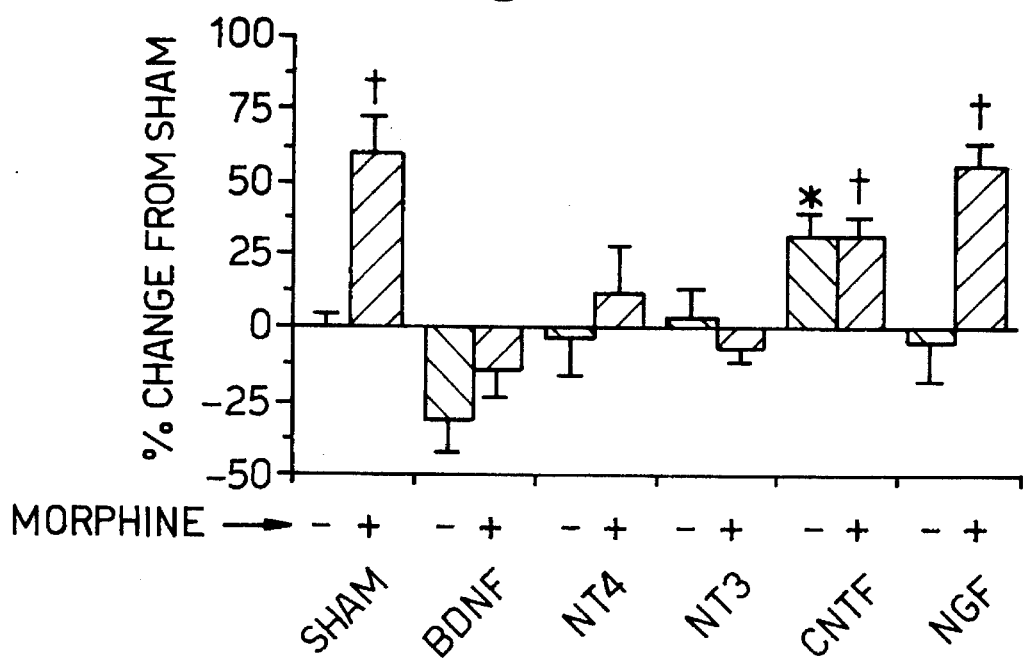
FIG. 1. Effect of neurotrophins on TH levels in the VTA: prevention of morphine induced changes. The X-axis denotes treatment group with (+) or (−) indicating the presence or absence of subcutaneous morphine treatment. The Y-axis denotes the relative values of TH expression as a percentage change from sham animals. Data are expressed as mean ± SEM (* $p<0.05$ versus sham [−morphine]; †$p<0.05$ versus sham [+morphine]). The number of animals used without morphine and with morphine, respectively, were: sham (7,8); BDNF (7, 8); NT-4 (8, 9); CNTF (4, 4); and NGF (12, 8).

The present invention is directed to a method for treating an addictive disease or disorder, comprising administering brain-derived neurotrophic factor (BDNF) or neurotrophin-4 (NT-4) to a subject believed to be suffering from or at risk for the addictive disease or disorder. Administration of BDNF or NT-4, or both, can modulate a behavior associated-with an addictive disease or disorder. BDNF and NT-4 function in this regard by opposing the biochemical and physiological changes that accompany an addictive stimulus.

The term "oppose" as used herein means to inhibit or to reverse. Inhibition refers to the ability to prevent the biochemical and physiological consequences of addictive stimuli, e.g., that occur upon administration of a drug of addiction. Reversing a biochemical or physiological change involves returning to the biochemical and phsyiological state that existed prior to onset of the addictive disease or disorder. In can be readily appreciated that the ability to reverse some of the biochemical and physiological changes associated with an addictive disease or disorder is a powerful therapeutic tool.

As used herein, the term "brain-derived neurotrophic factor" refers to a polypeptide that demonstrates the functional activity of brain-derived neurotrophic factor, e.g., as described in U.S. Pat. No. 5,229,500 and 5,180,820, as noted above.

The term "neurotrophin-4" refers to a polypeptide that demonstrates the functional activity of neurotrophin-4, e.g., as described in International Patent Publication WO 93/25684, published Dec. 23, 1993, U.S. patent application Ser. No. 07/898,194, filed Jun. 12, 1992, U.S. patent application Ser. No. 07/791,924, filed Nov. 14, 1991, and Fandl et al., 1994, J. Biol. Chem. 269:755–759, each of which is incorporated herein by reference in its entirety.

Thus, either polypeptide may be the natural protein as obtained from animal sources, such as, but not limited to human, ovine, porcine, murine, or rat sources. The term also refers to recombinant proteins expressed from genes encoding such protein. The recombinant protein may have the same post-translational modifications as the native proteins, or may be differently modified, e.g., by expression in prokaryotic expression systems, in which the polypeptide will not be glycosylated; expression in yeast expression systems, in which the polypeptide may be decorated with a yeast polysaccharide; or expression in a mammalian expression system, in which native or non-native glycosylation is possible. Similarly, analogs of the naturally occurring protein, e.g., that contain conservative amino acid substitutions, or that contain one or more non-peptide bonds, are also contemplated. Derivatives of the polypeptide, i.e., chemically modified forms of the natural protein, or analogs thereof, such as by conjugation to a targeting molecule to target the polypeptide across the blood brain barrier (such as transferrin), conjugation to a hydrophobic peptide or a fatty acid chain to facilitate transport across the blood brain barrier, phosphorylation, carboxymethylation, N-terminal acetylation, or other derivitizations, are also contemplated. Finally, the polypeptide may be a truncated form of the natural protein, or analog or derivative thereof, provided the truncated form demonstrates a neurotrophic functional activity.

As used herein, the terms "functional activity," "functionally active," and "neurotrophic functional activity" refer to a property of a polypeptide to modulate target cell phenotype or activity.

As used herein, the term "addictive disease or disorder" refers to a disease or disorder in which the subject has an extreme craving or compulsion to repeat a particular behavior. The present invention is particularly directed to therapeutic treatment of a drug addiction. Although almost any drug is capable of addiction, certain drugs demonstrated a marked propensity to become addictive. These include opiates (opium, morphine, heroin, and so called "designer drugs," which are opiates that have been chemically modified to avoid literal violation of the controlled substance laws, or to create a better or different psychophysiological effect), methadone, cocaine, nicotine, alcohol, certain depressants, and certain stimulants. Notwithstanding the specifically exemplified ability of the present invention to modulate the biochemistry and behavior that correlate with drug abuse, the invention further extends to the treatment of addictive psychological diseases or disorders, such as, but not limited to, obsessive-compulsive disease.

Accordingly, the invention provides pharmaceutical compositions for administration of BDNF or NT-4 according to the invention. Certain of such compositions are defined in the patents and patent applications referred to above. The invention further contemplates preparation of specific formulations or drug delivery systems, as discussed in greater detail infra, for administration of BDNF or NT-4, or both, to treat an addictive disease or disorder.

A composition comprising "A" (where "A" is a single molecule, such as a protein) is substantially free of "B" (where "B" comprises one or more contaminating proteins, or other contaminants) when at least about 75% by weight of the composition is "A". Preferably, "A" comprises at least about 90% by weight of the A+B species in the composition, most preferably at least about 99% by weight. It is also preferred that a composition, which is substantially free of contamination, contain only a single molecular weight species of each of the defined components having the activity or characteristic of interest.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host. Preferably, the activity so modified or modulated according to the invention is a behavioral activity. In particular, the behavioral activity may be locomotor activity, conditioned place preference, or drug self-administration.

Various abbreviations are used throughout the specification, which are defined as follows:

BDNF—brain-derived neurotrophic factor;
CNTF—ciliary neurotrophic factor;
GFAP—glial fibrillary acidic protein;
NAc—nucleus accumbens;
NFs—neurofilament proteins;
NGF—nerve growth factor;
NT-4—neurotrophin 4;
TH—tyrosine hydroxylase;
VTA—ventral tegmental area.

Additional terms relating to recombinant technology are defined as follows:

A "replicon" is any genetic element (e.g., plasmid, chromosome, virus) that functions as an autonomous unit of DNA replication in vivo, i.e., capable of replication under its own control.

A "vector" is a replicon, such as plasmid, phage or cosmid, to which another DNA segment may be attached so as to bring about the replication of the attached segment.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

"Heterologous" DNA refers to DNA not naturally located in the cell, or in a chromosomal site of the cell. Preferably, the heterologous DNA includes a gene foreign to the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A "promoter sequence" is a DNA regulatory region capable of binding RNA polymerase in a cell and initiating transcription of a downstream (3' direction) coding sequence.

A coding sequence is "under the control" of transcriptional and translational control sequences in a cell when RNA polymerase transcribes the coding sequence into mRNA, which is then trans-RNA spliced and translated into the protein encoded by the coding sequence.

The invention is based, in part, on the observation that some, but not all, neurotrophins oppose the effects of addictive stimuli on the biochemistry and neurophysiology of the brain, in particular, the VTA and NAc. In particular, it was observed that administration of BDNF or NT-4 could prevent or reverse the effects of morphine on the VTA and NAc of rat brain. Similarly, BDNF was observed to prevent the effects of cocaine on the VTA. Moreover, administration of BDNF or NT-4 reversed some of the behaviors associated with addiction. For example, administration of BDNF or NT-4 resulted in modification of behaviors such as locomotor activity, conditioned place preference, and drug self-administration in rats treated with morphine.

In contrast to the effects of BDNF and NT-4, neither CNTF nor NGF demonstrated an ability to modify the affects of addictive stimuli, such as morphine and cocaine.

These and additional aspects of the instant invention are presented in greater detail in the following description, which is arranged in sections relating to BDNF, NT-4, pharmaceutical compositions, and methods of administration, for clarity.

Brain-Derived Neurotrophic Factor (BDNF)

As discussed above, the term "BDNF" encompasses the native protein from an animal source, and functionally active derivatives, analogs and fragments thereof. In a preferred aspect, the BDNF is a polypeptide having the primary structure of human BDNF. However, the invention contemplates use of BDNF from other species, in particular rat, pig, and chicken. Amino acids sequences of BDNF from various species, including human, and methods for obtaining recombinant BDNF, a fully described in U.S. Pat. No. 5,229,500 and No. 5,180,820, discussed supra.

Neurotrophin-4 (NT-4)

As discussed above, the term "NT-4" encompasses the native protein from an animal source, and functionally active derivatives, analogs and fragments thereof. In a preferred aspect, the NT-4 is a polypeptide having the primary structure of human NT-4. However, the invention contemplates use of NT-4 from other species, in particular rat, pig, and chicken. Amino acids sequences of NT-4 from various species, including human, and methods for obtaining recombinant NT-4, a fully described in International Patent Publication WO 93/25684, published Dec. 23, 1993, U.S. patent application No. 07/898,194, filed Jun. 12, 1992, and U.S. patent application No. 07/791,924, filed Nov. 14, 1991, each of which is incorporated herein by reference it its entirety.

Neurotrophin Chimeras

In addition to BDNF and NT-4, chimeric proteins comprising functionally active portions of BDNF, or NT-4, or both can be used to oppose the biochemical and physiological effects of addictive diseases or disorders. For example, such constructs are described in U.S. Pat. No. 5,169,764, issued Dec. 8, 1992, entitled "MULTITROPHIC AND MULTIFUNCTIONAL CHIMERIC NEUROTROPHIC FACTORS, AND NUCLEIC ACIDS AND PLASMIDS ENCODING THE CHIMERAS."

Therapeutic Compositions

The present invention further contemplates formulating BDNF or NT-4, or both, in pharmaceutically acceptable carrier to facilitate transport across the blood brain barrier, in order to allow for systemic administration of the pharmaceutical composition. In particular, the invention contemplates liposome preparations, which may facilitate transport across the blood brain barrier (see Langer, 1990, Science 249: 1527–1533; Treat et al., 1989, In *Liposomes in the Therapy of Infectious Disease and Cancer*, Lopez-Berestein and Fidler (eds.), Liss, New York, pp. 353–365; Lopez-Berestein, ibid., pp. 317–327; see generally ibid.).

Methods for Treating or Preventing an Addictive Disease

The present invention provides for administration of an amount of BDNF or NT-4, or both, effective to treat or prevent an addictive disease or disorder in a subject. Preferably the subject is a human, however, as animals in addition to humans may demonstrate addictive diseases or disorders, whether resulting from addiction to opiates or other drugs subsequent to a veterinary procedure or as a result of a psychological disorder, such as an obsessive compulsive-type of disorder, the invention can be used in birds, such as chickens, turkeys, and pets; in mammals, including but not limited to domesticated animals (canine and feline); farm animals (bovine, ovine, equine, caprine, porcine, and the like); rodents; and undomesticated animals.

Similarly, BDNF or NT-4, or both, can be administered prophylactically in order to prevent the biochemical and physiological, and associated behavioral, consequences of administration of an addictive drug. For example, where a surgical procedure or injury will result in pain of such magnitude that opiate, e.g., morphine, are required to control the pain, either BDNF or NT-4, or both, can be administered as described below prior to or concurrently with the addictive drug. As shown in a specific example, infra, either BDNF or NT-4 can inhibit the biochemical changes associated with administration of morphine or cocaine.

According to the invention, the addictive disease or disorder may be treated or prevented by introducing the BDNF or NT-4, or combination thereof, by any parenteral route. As used herein, the term "parenteral" refers to introduction of the polypeptide by intravenous (i.v.), intraarterial (i.a.), intraperitoneal (i.p.), intramuscular (i.m.), intraventricular, intracranial, subcutaneous (s.c.), subdermal, oral, nasal, or rectal routes. Preferably, the route is intraventricular or intracranial.

BDNF or NT-4, or both, can be administered continuously, or daily in a bolus dose (b.d.). Preferably, the amount of polypeptide in circulation remains fairly stable, to avoid fluctuations that allow for the addictive craving to manifest itself in the subject. The amount of BDNF or NT-4 administered may vary from about 0.01 µg per kg of body weight per day (µg/kg/day) to about 100 mg/kg/day; preferably, from about 0.1 µg/kg/day to about 10/µg/kg/day. In a specific embodiment, infra, 2.5 µg/day were administered directly into the affected area of the brain of rats. The actual dosage regimen will depend on the route of administration (systemic administration requiring a larger dose than administration to the brain, which in turn requires a larger dose than administration locally to the VTA), nature and severity of the addiction, the length of time a subject has been addicted, as well as the age, sex, weight, health, and other characteristics of the individual subject. A physician of ordinary skill in the art will account for these variations in determining the appropriate dosage and regimen by following good medical practice and standard pharmacological procedures.

In yet another embodiment, the therapeutic compound can be delivered in a controlled release system. In one embodiment, a pump may be used (see Langer, 1990, Science 249:1527–1533; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, 1983, J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled release system can be placed in the brain, preferably in proximity of the therapeutic target, i.e., the VTA, thus requiring only a fraction of the systemic dose, and avoiding side effects (see, e.g., Goodson, 1984, In *Medical Applications of Controlled Release*, vol. 2, pp. 115–138). Other controlled release systems are discussed in the review by Langer (supra).

In another embodiment, administration of BDNF or NT-4 can be accomplished by transient or long term gene therapy, or by implanting cells transfected with a BDNF or NT-4 expression vector, e.g., by direct transplantation of homologous cells, or by incorporating homologous or non-homologous cells in an appropriate matrix for implantation. Accordingly, the present invention provides for introduction of a vector containing a gene encoding BDNF or NT-4, or both, in vivo to provide for increased expression of BDNF or NT-4. More preferably, the vector is introduced for expression in brain cells, most preferably in cells of the VTA. Genes encoding BDNF and NT-4, suitable vectors containing such genes, and transfected cells capable of expressing such proteins are described in U.S. Pat. No. 5,229,500 and No. 5,180,820 (BDNF), and International Patent Publication WO 93/25684 (NT-4).

Many methods are known in the art for introducing a transgene in vivo, including transfection of neural cells. In one embodiment, the gene encoding BDNF or NT- 4 may be introduced in vivo in a vital vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective,vital vectors allows for administration to cells in a specific, localized area, without concern that the vector can infect other cells. Thus, a particular locus, e.g., in the brain or spinal chord, can be specifically targeted with the vector. In a specific embodiment, a defective herpes virus 1 (HSV1) vector may be used (Kaplitt et al., 1991, Molec. Cell. Neurosci. 2:320–330). In another embodiment, the viral vector is an attenuated adenovirus vector, such as the vector described by Stratford-Perricaudet et al. (1992, J. Clin. Invest. 90:626–630 ). In a yet a further embodiment, the vector is a defective adeno-associated virus vector (Samulski et al., 1987, J. Virol. 61:3096–3101; Samulski et al., 1989, J. Virol. 63:3822–3828). Surprisingly, the adenovirus and adeno-associated virus vectors have been found to be effective in transfecting neurons. For example, the AAV vector can be used to express the lacZ gene in neurons.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of the BDNF or NT-4 vector (Felgner, et. al., 1987, Proc. Natl. Acad. Sci. U.S.A. 84:7413–7417; see Mackey, et al., 1988, Proc. Natl. Acad. Sci. U.S.A. 85:8027–8031)). The use of cationic lipids may promote encapsulation of negatively charged nucleic acids, and also promote fusion with negatively charged cell membranes (Felgner and Ringold, 1989, Science 337:387–388). Lipofection into the nervous system in vivo has recently been achieved (Holt, et. al., 1990, Neuron 4:203–214). The use of lipofection to introduce exogenous genes into the nervous system in vivo has certain practical advantages. Molecular targeting of liposomes to specific cells represents one area of benefit. It is clear that directing transfection to limited neuronal types, particularly the VTA, would be particularly advantageous in a tissue with such cellular heterogeneity as the brain. Lipids may be chemically coupled to other molecules for the purpose of targeting (see Mackey, et. al., 1988, supra). Targeted peptides, e.g., hormones or neurotransmitters, and proteins such as antibodies, or non-peptide molecules could be coupled to liposomes chemically.

It is also possible to introduce the vector in vivo as a naked DNA plasmid, e.g., through a cut or pierced axon. Retrograde axonal transport of the vector may be enhanced by coupling the plasmid to an appropriate carrier, which normally undergoes retrograde, rather than antegrade, transport.

In another embodiment, the vector containing the gene encoding BDNF or NT-4 can be introduced via a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

Long term or transient expression of the BDNF or NT-4 protein will depend on the choice of vector, whether the vector integrates in the host genome, and the choice of promoter.

Preparation of such vectors, which contain a gene encoding BDNF or NT-4 operatively associated with an expression control sequence, i.e., a promoter, with or without additional control sequences, e.g., an inducible element, an enhancer, etc., is well known in the art (e.g., Sambrook, Fritsch & Maniatis, "Molecular Cloning: A Laboratory Manual," Second Edition [1989][Cold Spring Harbor Laboratory Press, Cold Spring Harbor, N.Y. [herein "Sambrook et al., 1989"]; "DNA Cloning: A Practical Approach," Volumes I and II [D. N. Glover ed. 1985]; "Oligonucleotide Synthesis" [M. J. Gait ed. 1984]; "Nucleic Acid Hybridization" [B. D. Hames & S. J. Higgins eds. 1985]; "Transcription And Translation" [B. D. Hames & S. J. Higgins, eds. 1984]; "Animal Cell Culture" [R. I. Freshney, ed., 1986]; "Immobilized Cells And Enzymes" [IRL Press, 1986]; B. Perbal, "A Practical Guide To Molecular Cloning" [1984]).

Generally, BDNF or NT-4, or both, or transgenes capable of expressing these proteins, may be administered until the subject appears to have overcome the addictive disease or disorder. Preferably, the treatment is discontinued at that time. However, subjects suffering from or at risk for a constitutive addictive disease or disorder, such as but not limited to obsessive compulsive disorder, may require treatment on a permanent or long term basis.

For prevention of addiction, administration of BDNF or NT-4, or both, should precede or accompany administration of the addictive agent, e.g., narcotic drug, and should continue until administration of the addictive agent ceases. Preventive treatment with BDNF or NT-4, or both, may continue past the point of administration of the addictive agent to prevent any of the associated biochemical or physiological changes, or coordinate behavioral changes.

The present invention may be better understood by reference to the following non-limiting example, which is provided by way of exemplification.

EXAMPLE: BDNF AND NT-4 OPPOSE THE EFFECTS OF MORPHINE AND COCAINE

This example demonstrates the ability of the neurotrophic factors BDNF and NT-4 to oppose, i.e., inhibit or reverse, or both, the effects of drugs of addiction on the expression of tyrosine hydroxylase and glial fibrillary acidic protein.

Materials and Methods

Male Sprague-Dawley rats (~260–275 g; CAMM, Wayne, N.J.) were used in these studies. Morphine and cocaine were administered systemically. Morphine was administered as the daily implantation of subcutaneous pellets (containing 75 mg of morphine base; National Institute on Drug Abuse) while rats were under light halothane anesthesia daily for 5 days. Cocaine was administered twice daily via intraperitoneal injections of cocaine hydrochloride (15 mg/kg), typically for 10 days with rats typically, used on day 11. Growth factor (BDNF, NT-4, ciliary neurotrophic factor [CNTF], or nerve growth factor [NGF]) or vehicle (10 mM phosphate buffer, pH 7.4, 1% BSA in 0.9% saline; negative control) was administered continuously directly into the VTA via osmotic mini-pumps (Alzet model 2002, which provide a constant infusion of 0.5 µl/hr for 14 days. BDNF, NT-4, and CNTF were provided by Regeneron Pharmaceuticals (Tarrytown, N.Y.); NGF was obtained from Genentech (San Francisco, Calif.).

Initial trial doses of neurotrophins at 12.5 µg/day, based on previous studies involving introduction of neurotrophins in vivo into the *substantia nigra* resulted in toxicity for some animals, which was confounded when morphine or cocaine was administered. A lower dose of 2.5 µg/day showed no apparent toxicity for BDNF, NT-4, NT-3, or NGF. However, CNTF infusions at 2.5/μg/day resulted in substantial weight loss and high mortality when administered with morphine, so a lower dose of 1.5 μg/day was used. This dose resulted in moderate weight loss, but without any other signs of impaired health. Thus, all animals received 2.5 μg/day of growth factor, except for CNTF, which was administered at 1.5 μg/day.

Animals were anesthetized with 3 ml/kg Equithesin and implanted with an osmotic pump connector cannula (28 gauge cannula, 22 gauge connector; Plastic Products Co.). Midline VTA coordinates of −5.3 mm A/P and 8.4 mm D/V were used. Reproducible placement was confirmed in preliminary experiments and confirmed in each animal at the time of dissection. Osmotic pumps were place subcutaneously between the scapulae and connected to the cannula via PE60 tubing cut to 2.5 cm length. Each end was sealed with LocTite glue. The cannula was secured in place with dental cement. Control rats were implanted with cannulae that had been sealed at the connector end with LocTite glue. Studies were performed comparing this set of control rats to rats implanted with an osmotic pump containing the vehicle solution without any growth factor. There were no significant differences in the biochemical parameters measured between these two control groups.

One of three experimental paradigms were used. In the first, designated "morphine prevention," growth factor or vehicle administration was begun on day 1, morphine or placebo pellet administration was performed on day 6 through day 10, and rats were sacrificed and examined on day 11. In the second paradigm, designated "morphine reversal," morphine pellets were administered on day 1 through day 5, growth factor or vehicle treatment was initiated on day 6 and continued through day 15, and rats were examined on day 16. In the third paradigm, designated "cocaine prevention," growth factor (or vehicle) and cocaine treatments were initiated on day 1, and rats were examined on day 11.

Following in vivo treatment, the rats were sacrificed by decapitation. Brains were removed and cooled in ice-cold physiological buffer. The ventral tegmental area (VTA), the nucleus accumbens (Nac), and substantia nigra (SN) were removed as 15 (VTA or SN) and 12 gauge punches (NAc) from 1 mm coronal sections of brain. Brain samples were homogenized in 125 μl of 1% SDS. Samples were immunoblotted to measure levels of TH, GFAP, and neurofilaments (NFs). Rabbit polyclonal antiserum for TH (Dr. John W. Haycock, Louisiana State University) was used at a 1:10,000 dilution; murine monoclonal antibodies for GFAP and NFs were obtained from Sigma and used at a dilution of 1:2000. Peroxidase-labeled secondary antibodies from vector were used and detected via enhanced chemiluminescence (ECL, Amersham) and autoradiography. The resulting autoradiograms were quantified via a Macintosh-based image analysis system with NIH image 5.2 software.

The NAc punches were assayed for cyclic-AMP-dependent protein kinase and adenylyl cyclase activity in pairs. The punches were homogenized in a solution of 200 μl of 50 mM Tris (pH 7.4), 1 mM dithiothreitol, 1 mM EDTA, 10 μg/ml leupeptin, and 50 kallikrein units/ml aprotinin. Duplicate aliquots of homogenates (containing 5–10 μg protein) were centrifuged in a Savant microfuge at 8,000×g and resulting pellets were assayed for adenylyl cyclase activity. Enzyme activity was determined under :basal conditions and in the presence of GTP (100 μM) plus forskolin (5 μM). The specific activities of adenylyl cyclase in the NAc from control animals were similar to values reported previously (Terwilliger et al., 1991).

For protein kinase activity assays, aliquots of NAc homogenates were centrifuged in a Sorvall microultracentrifuge at 150,000×g for 10 min. at 4° C. The resulting pellets, designated the particulate fractions, were resuspended in the original volume of homogenization buffer. Duplicate aliquots of the fractions (containing 2–5 μg of protein) were assayed for PKA activity by use of a filter paper assay with purified histone as substrate as described (Terwilliger et al., supra). PKA activity was calculated as the difference in histone phosphorylation observed in the presence of cAMP and that measured in the presence of protein kinase inhibitor, a specific PKA inhibitor. Under the assay conditions use, PKA activity was linear over a 5-fold range of tissue concentration and between 1 and 5 min of incubation. The specific activities of PKA in particulate fractions of the NAc from control animals were similar to values reported previously.

Any residual morphine that might have been present in particulate fractions of brain tissue did not influence the final determinations of adenylyl cyclase or PKA activities. Thus, inclusion of naloxone (100 μM) in the assay did not affect enzyme activities in the NAc.

Results

These data relate to the actions of neurotrophins on the mesolimbic dopamine system of rats. Growth factors were directly injected in the VTA, a site of significant neurophysiological plasticity associated with drug abuse and addiction.

BDNF and NT-4 both prevented and reversed the ability of morphine to increase levels of TH and GFAP in the VTA region, compared to controls. Infusions of CNTF or NGF into the VTA failed to produce these effects; administration of these growth factors yielded no differences from control in this assay.

The effects of administration of growth factors prior to morphine or placebo are shown in FIG. 1. The level of expression of TH in the VTA increased more than 50% in morphine-treated rats. BDNF, NT-4, and NT-3 greatly reduced the level of expression of TH. CNTF had no effect on the animals that received morphine; however, this factor caused a greater than 25% increase in the level of TH expression in rats that had not been treated with morphine. It was observed previously that CNTF mimicked the changes induced by morphine (Beitner-Johnson et al., 1993, Soc. Neurosci. Abs. 19:633), without having any additive effect with morphine.

Figure 2:
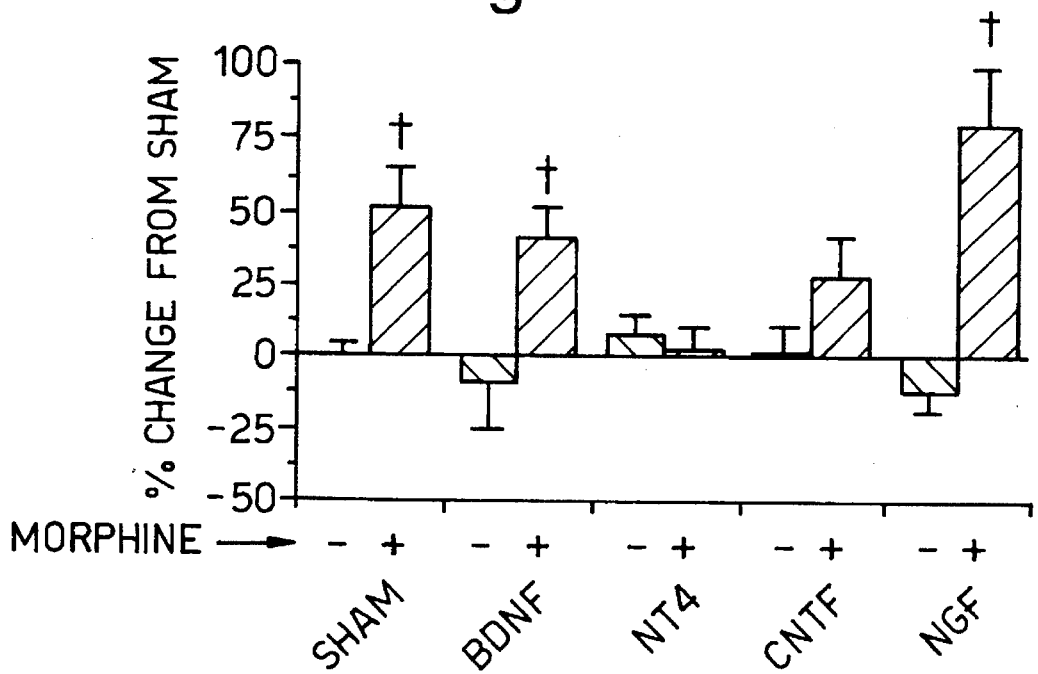
FIG. 2. Effect of neurotrophins on GFAP levels in the VTA: prevention of morphine induced changes. The X and Y-axes denote the same information as in FIG. 1, with the same p values, except that Y is the relative value of GFAP expression. The number of animals used without and with morphine, respectively, were: sham (8, 8); BDNF (7, 8); NT-4 (8, 9); NT-3 (9, 8); CNTF (4, 4); and NGF (12, 8).

Similar effects of neurotrophins were observed on the level of expression of GFAP in the VTA (FIG. 2). Control animals had a greater than 50% increase in the level of GFAP after administration of morphine. Animals treated with BDNF did not show as much of an increase, and animals treated with NT-4 demonstrated almost no increase with morphine.

Figure 3:
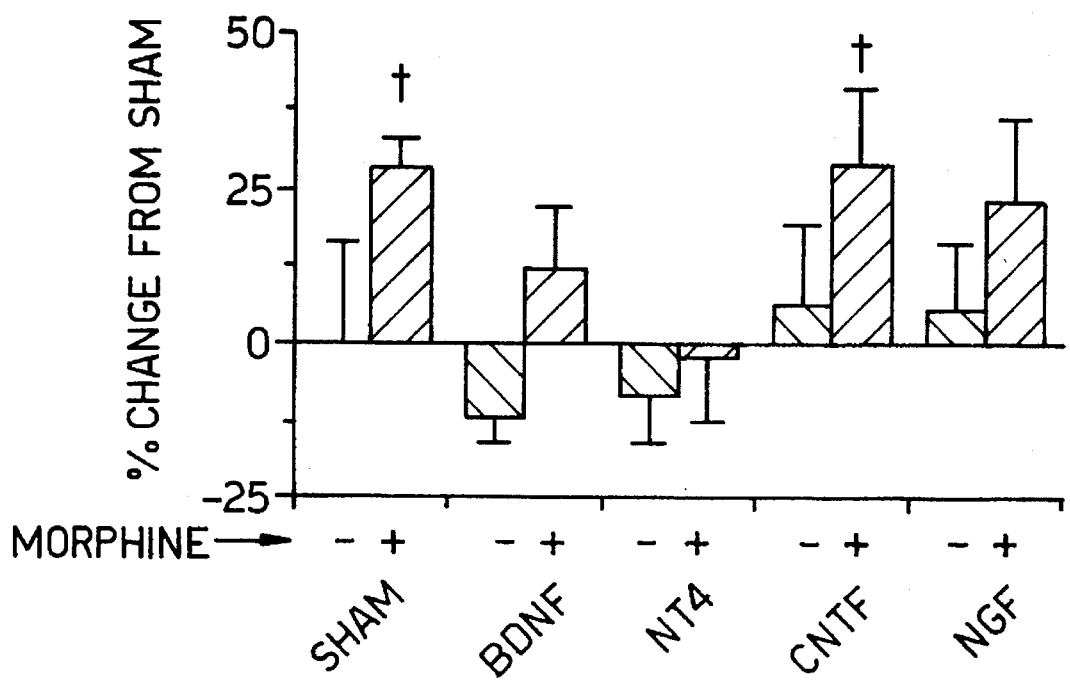
FIG. 3. Effect of neurotrophins on PKA activity in the NAc. The X and Y axes denote the same information as in FIG. 1, with the same p values, except that Y is the relative value of PKA activity. The number of animals used without and with morphine, respectively, were: sham (6, 4); BDNF (9, 8); NT-4 (9, 8); CNTF (7, 3); and NGF (7, 3).
Figure 4:
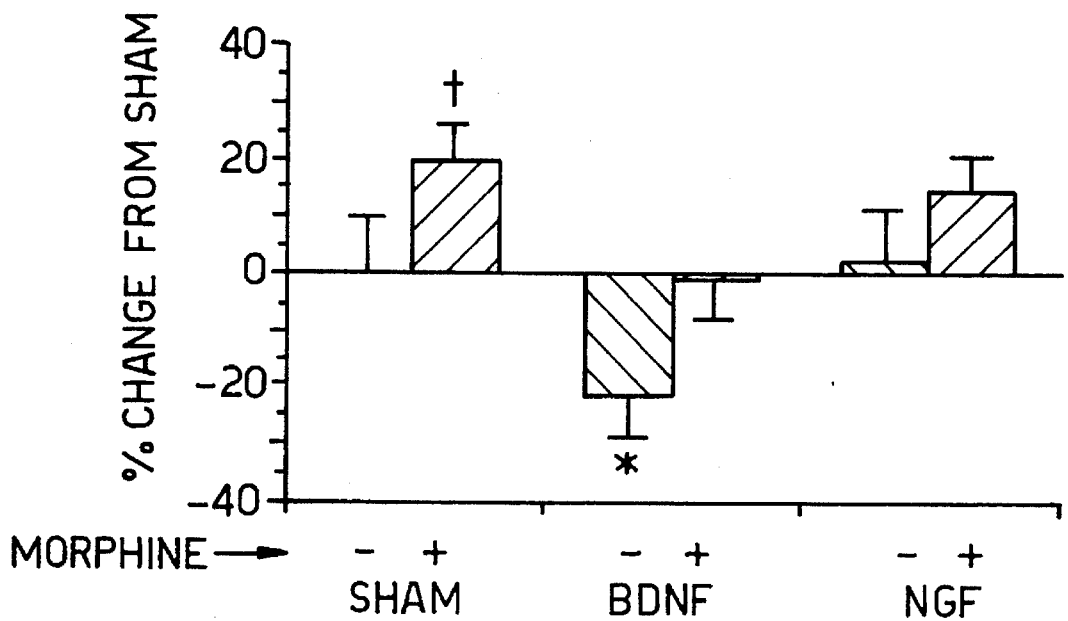
FIG. 4. Effect of neurotrophins on adenylyl cyclase activity in the NAc. The X and Y axes denote the same information as in FIG. 1, with the same p values, except that Y is the relative value of adenylyl cyclase activity. The number of animals used without and with morphine, respectively, are: sham (4, 4); BDNF (5, 6); and NGF (4, 4).

Similarly, administration of BDNF or NT-4, but not CNTF or NGF, into the VTA also prevented the ability of morphine to increase levels of cyclic-AMP-dependent protein kinase in the NAc, compared to controls (administration of vehicle only). As shown in FIG. 3, both BDNF and NT-4 decreased the level of PKA activity in the NAc in response to morphine; CNTF and NGF had little or no effect on this parameter. Similarly, BDNF, but not NGF, decreased the level of adenylyl cyclase activity in the NAc (FIG. 4).

Figure 5:
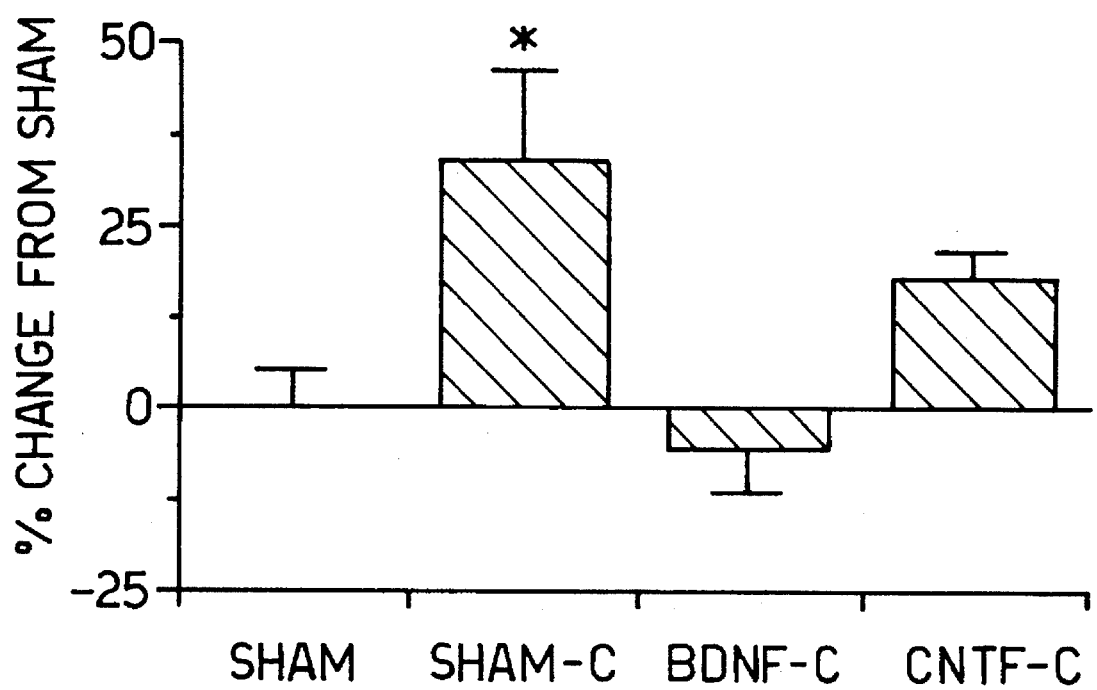
FIG. 5. Effect of neurotrophins on TH levels in the VTA: prevention of cocaine induced changes. The X and Y-axes denote the same information as in FIG. 1. C indicates concurrent cocaine treatment. Data are expressed as mean ± SEM (* p<0.05 versus sham [+cocaine]). The number of animals used were: sham (5); BDNF (8); and CNTF (5).

Comparable results were observed in the animals subjected to cocaine administration. Intra-VTA infusion of BDNF, but not CNTF, prevented the ability of repeated cocaine administration to increase levels of tyrosine hydroxylase in this brain region (FIG. 5).

Most significantly, preliminary observations indicate that administration of BDNF or NT-4 directly into the VTA can modify the behavioral actions of morphine or cocaine as measured by locomotor activity, conditioned place reference, or drug self-administration.

Conclusions

These novel data have important implications for developing pharmaceutical agents directed at the BDNF and NT-4 neurotrophin systems for use in treating addictive disorders. Based on the work described in this Example, it appears that BDNF or NT-4 administration, or both together, would both prevent and reverse some of the biochemical adaptations that drugs of abuse produce in the mesolimbic dopamine system that we believe represents part of the molecular basis of drug reinforcement and craving. In particular, administration of BDNF or NT-4 appears to reduce drug craving, which is critical for treatment of addictive disorders.

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims.

Various references are cited herein, the disclosures of which are incorporated by reference herein in their entirety.

What is claimed is:

1. A method for treating or preventing an addictive disease or disorder, comprising administering to a subject suspected of suffering from or at risk for an addictive disease or disorder an amount of brain-derived neurotrophic factor (BDNF) effective to oppose a biochemical or neurophysiological change that is associated with the addictive disease or disorder.

2. The method according to claim 1, wherein the BDNF is administered intraventricularly, intracranially, or in a device that has been implanted cranially.

3. The method according to claim 1, wherein the BDNF is administered continuously.

4. The method according to claim 1, wherein the subject is a human.

5. The method according to claim 4, wherein the BDNF is human BDNF.

6. The method according to claim 1, wherein the administration of BDNF effects a neurophysiological change to the ventral tegmental area (VTA) selected from the group consisting of opposing increased levels of tyrosine hydroxylase associated with the addictive disease or disorder, opposing increased expression of glial fibrillary acidic protein associated with the addictive disease or disorder, opposing decreased levels of neurofilament proteins associated with the addictive disease or disorder, and opposing increased levels of cyclic-AMP-dependent protein kinase activity in the nucleus accumbens.

7. The method according to claim 1, wherein the addictive disease or disorder is addiction to a drug of abuse.

8. The method according to claim 7, wherein the drug of abuse is a drug selected from the group consisting of morphine, a morphine derivative, heroin, a heroin derivative, methadone, opium, cocaine, a cocaine derivative, nicotine and alcohol.

9. The method according to claim 8, wherein the drug of abuse is morphine or cocaine.

10. The method according to claim 1, wherein the addictive disease or disorder is an obsessive-compulsive disorder.

11. A method for treating an addictive disease or disorder, comprising administering to a subject suspected of suffering from or at risk for an addictive disease or disorder an amount of neurotrophin-4 (NT-4) effective to oppose a biochemical or neurophysiological change that is associated with the addictive disease or disorder.

12. The method according to claim 11, wherein the NT-4 is administered intraventricularly, intracranially, or in a device that has been implanted cranially.

13. The method according to claim 11, wherein the NT-4 is administered continuously.

14. The method according to claim 11, wherein the subject is a human.

15. The method according to claim 14, wherein the NT-4 is human NT-4.

16. The method according to claim 11, wherein the administration of NT-4 effects a neurophysiological change to the ventral tegmental area (VTA) selected from the group consisting of opposing increased levels of tyrosine hydroxylase associated with the addictive disease or disorder, opposing increased expression of glial fibrillary acidic protein associated with the addictive disease or disorder, opposing decreased levels of neurofilament proteins associated with the addictive disease or disorder, and opposing increased levels of cyclic-AMP-dependent protein kinase activity in the nucleus accumbens.

17. The method according to claim 11, wherein the addictive disease or disorder is addiction to a drug of abuse.

18. The method according to claim 17, wherein the drug of abuse is a drug selected from the group consisting of morphine, a morphine derivative, heroin, a heroin derivative, methadone, opium, cocaine, a cocaine derivative, nicotine, and alcohol.

19. The method according to claim 18, wherein the drug of abuse is morphine or cocaine.

20. The method according to claim 11, wherein the addictive disease or disorder is an obsessive-compulsive disorder.

* * * * *

UNITED STATES PATENT AND TRADEMARK OFFICE
CERTIFICATE OF CORRECTION

PATENT NO. : 5,556,837
DATED : September 17, 1996
INVENTOR(S) : Eric J. Nestler, et al.

It is certified that error appears in the above-identified patent and that said Letters Patent is hereby corrected as shown below:

Column 1, line 8, insert the following information:

The invention identified above is a subject invention under 35 U.S.C. 200, et seq., and the Standard Patent Rights Clause at 37 C.F.R. 401.14 or F.A.R. 52.227-11, which are included among the terms of the above-identified grant/contract award from the Public Health Service/National Institutes of Health.

Signed and Sealed this

Thirteenth Day of April, 1999

Attest:

Q. TODD DICKINSON

*Attesting Officer*       *Acting Commissioner of Patents and Trademarks*